United States Patent
Jinde et al.

(10) Patent No.: US 8,500,638 B2
(45) Date of Patent: Aug. 6, 2013

(54) NON-CONTACT ULTRASONIC TONOMETER

(75) Inventors: Masayuki Jinde, Gamagori (JP);
Tetsuyuki Miwa, Nukata-gun (JP);
Kenichiro Makino, Gamagori (JP)

(73) Assignee: Nidek Co., Ltd., Gamagori-Shi (JP)

( * ) Notice: Subject to any disclaimer, the term of this patent is extended or adjusted under 35 U.S.C. 154(b) by 168 days.

(21) Appl. No.: 12/659,617

(22) Filed: Mar. 15, 2010

(65) Prior Publication Data
US 2010/0249569 A1  Sep. 30, 2010

(30) Foreign Application Priority Data

Mar. 31, 2009 (JP) .................. 2009-087599
Sep. 28, 2009 (JP) .................. 2009-222049
Dec. 11, 2009 (JP) .................. 2009-281376

(51) Int. Cl.
*A61B 5/00* (2006.01)

(52) U.S. Cl.
USPC ........................................................ 600/398

(58) Field of Classification Search
USPC ................................. 600/398–402
See application file for complete search history.

(56) References Cited

U.S. PATENT DOCUMENTS

| | | | |
|---|---|---|---|
| 5,287,331 A | | 2/1994 | Schindel et al. |
| 6,607,527 B1 * | | 8/2003 | Ruiz et al. ........... 606/41 |
| 2003/0088169 A1 | | 5/2003 | Percival et al. |
| 2004/0193033 A1 * | | 9/2004 | Badehi et al. ........... 600/402 |
| 2004/0260168 A1 * | | 12/2004 | Shimmyo ........... 600/399 |

FOREIGN PATENT DOCUMENTS

| | | |
|---|---|---|
| CN | 1607924 A | 4/2005 |
| DE | 10 2006 033 035 A1 | 1/2008 |
| EP | 0 371 590 A1 | 6/1990 |
| EP | 2 022 392 A2 | 2/2009 |
| JP | A-2005-506783 | 3/2005 |
| WO | WO 93/13705 A1 | 7/1993 |
| WO | WO 94/23642 A1 | 10/1994 |
| WO | WO 03/035281 A2 | 5/2003 |
| WO | WO 2008/072527 A1 | 6/2008 |

OTHER PUBLICATIONS

Aug. 25, 2011 Office Action issued in European Patent Application No. 10 157 382.2.

Jinde, M. et al., "Development of a new non-contact intraocular pressure measurement system using a phase shift method," *Conference of Institute of Electrical Engineers, Sensors and Micromachines Division*, 2007, pp. 93-96 (with translation).

May 26, 2010 European Search Report issued in corresponding European Patent Application No. 10 157 382.2.

* cited by examiner

*Primary Examiner* — Max Hindenburg
(74) *Attorney, Agent, or Firm* — Oliff & Berridge, PLC

(57) ABSTRACT

A non-contact ultrasonic tonometer for measuring an intraocular pressure of an examinee's eye in non-contact manner by use of an ultrasonic wave, comprises: an ultrasonic transducer including a transmitter which emits an ultrasonic transmission pulse wave to the eye and a receiver which detects an ultrasonic reflection pulse wave from the eye, the transducer being arranged to be placed in a position apart from the eye and to transmit and receive the pulse wave with respect to the eye through the medium of air; and a calculation part being arranged to obtain a peak amplitude level of the reflection pulse wave based on an output signal from the ultrasonic transducer and measure the intraocular pressure based on the obtained peak amplitude level.

7 Claims, 11 Drawing Sheets

| P1\h | P1(A) | P1(B) | P1(C) | ...... | ...... |
|---|---|---|---|---|---|
| h(A) | Pc(A,A) | Pc(A,B) | Pc(A,C) | ...... | ...... |
| h(B) | Pc(B,A) | Pc(B,B) | Pc(B,C) | ...... | ...... |
| h(C) | Pc(C,A) | Pc(C,B) | Pc(C,C) | ...... | ...... |
| ⋮ | ⋮ | ⋮ | | | |
| ⋮ | ⋮ | ⋮ | | | |
| ⋮ | ⋮ | ⋮ | | | |

NON-CONTACT ULTRASONIC TONOMETER

CROSS-REFERENCE TO RELATED APPLICATIONS

This application is based upon and claims the benefit of priority from each of the prior Japanese Patent Applications No. 2009-87599 filed on Mar. 31, 2009, No. 2009-222049 filed on Sep. 28, 2009, and No. 2009-281376 filed on Dec. 11, 2009, the entire contents of which are incorporated herein by reference.

TECHNICAL FIELD

The present invention relates to a non-contact ultrasonic tonometer for measuring the intraocular pressure (IOP) of an examinee's eye in a non-contact manner by ultrasound (an ultrasonic wave).

BACKGROUND ART

Recently, there is proposed an apparatus including a probe having a vibrator which emits an ultrasonic wave toward a cornea of an examinee's eye and a sensor for detecting the ultrasonic wave reflected by the cornea to measure the IOP of the eye in non-contact manner (see Patent Literature 1).

In the case where output signals from the probe are processed to obtain the IOP, conventionally, the IOP is determined based on a frequency shift amount of a reflected wave with respect to an incident wave.

CITATION LIST

Patent Literature
Patent Literature 1: WO2008/072527

SUMMARY OF INVENTION

Technical Problem

However, in the conventional calculation method, even when a distance (a working distance) between the examinee's eye and the probe in forward and backward directions slightly is changed, the frequency shift amount is likely to greatly vary. Such changes in working distance may affect a measured value. Therefore, very strict adjustment of the working distance is required.

In an actual measurement of a human eye, it is predicted that the working distance changes depending on movements of the eye, which may cause variations in measured values. Furthermore, strict alignment with the human eye is regarded as leading to a prolonged measurement time. This is a large burden on an examiner and an examinee.

The present invention has been made in view of the above circumstances and has a purpose to provide an non-contact ultrasonic tonometer capable of stably measuring the IOP of an examinee's eye by reducing variations in measurement results due to changes in a working distance.

Solution to Problem

To achieve the above purpose, one aspect of the present invention provides a non-contact ultrasonic tonometer for measuring an intraocular pressure of an examinee's eye in non-contact manner by use of an ultrasonic wave, comprising: an ultrasonic transducer including a transmitter which emits an ultrasonic transmission pulse wave to the eye and a receiver which detects an ultrasonic reflection pulse wave from the eye, the transducer being arranged to be placed in a position apart from the eye and to transmit and receive the pulse wave with respect to the eye through the medium of air; and a calculation part being arranged to obtain a peak amplitude level of the reflection pulse wave based on an output signal from the ultrasonic transducer and measure the intraocular pressure based on the obtained peak amplitude level.

Advantageous Effects of Invention

According to the invention, it is possible to stably measure the IOP of an examinee's eye by reducing variations in measurement results due to changes in a working distance.

DESCRIPTION OF EMBODIMENTS

Figure 1:
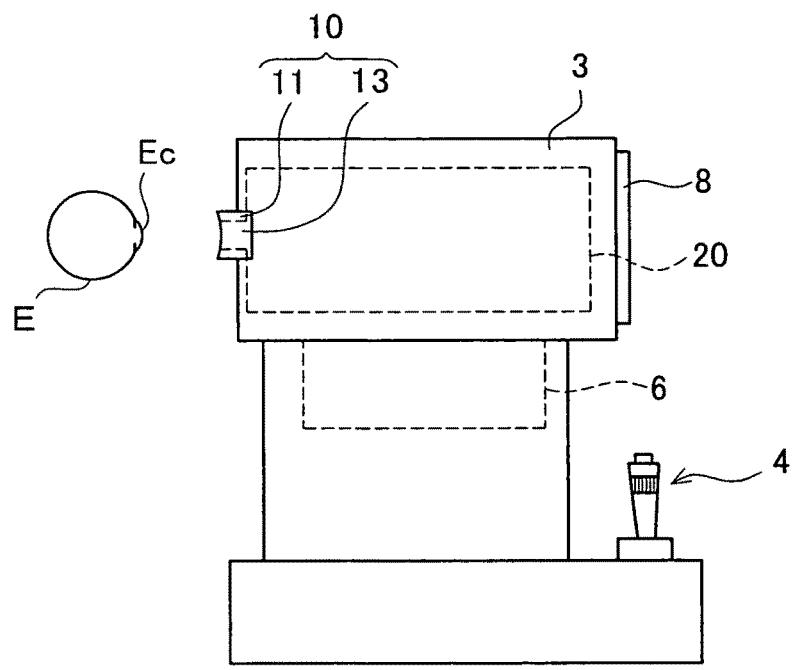
FIG. 1 is a schematic external view of a non-contact ultrasonic tonometer in an embodiment.
Figure 2:
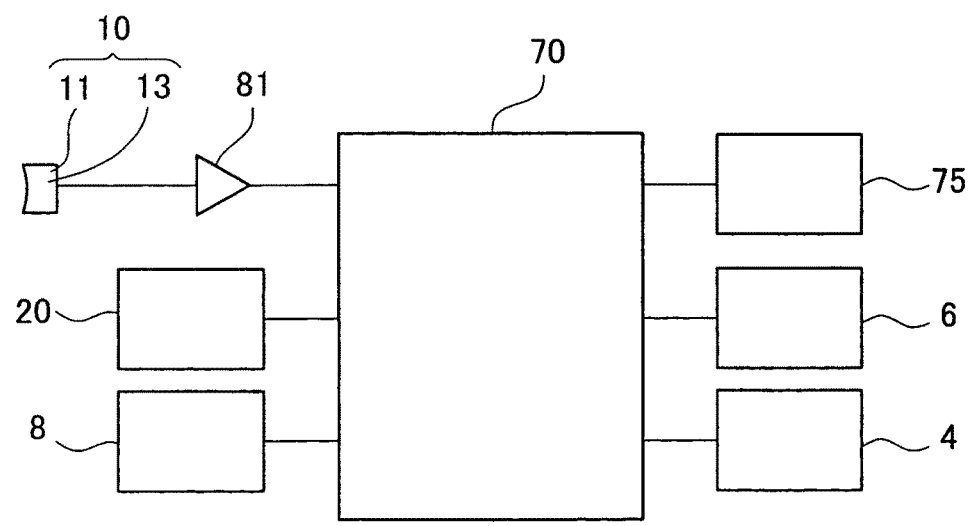
FIG. 2 is a schematic block diagram of a control system of the tonometer.

A detailed description of a preferred embodiment of the present invention will now be given referring to the accompanying drawings. FIG. 1 is a perspective external view of a non-contact ultrasonic tonometer in this embodiment. FIG. 2 is a schematic block diagram of a control system of the tonometer.

In FIG. 1, a main unit (a main body) 3 is provided with a probe (a transducer) 10 placed in a position apart from an examinee's eye and an observation optical system 20 including an imaging device to observe an anterior segment of the eye E. In a housing of the main unit 3, there are arranged an alignment optical system, a fixation optical system, and others, which are not shown. A monitor 8 displays an image of the anterior segment imaged by an imaging device of the observation optical system 20, measurement results, and others. When an examiner manipulates a joystick 4 while observing the anterior segment image displayed on the monitor 8, a drive part 6 is driven based on such a manipulate signal to move the main unit 3 in three dimensions. In this way, the main unit 3 is aligned with respect to the eye E.

The probe 10 emits ultrasonic pulses toward a cornea Ec of the eye E through the medium of air and also detects the ultrasonic pulses reflected by the cornea Ec as a reflected wave. The probe 10 includes a vibrator (an ultrasonic transmitter) 11 for emitting an ultrasonic wave (an incident wave) which will enter the eye E and a vibration detecting sensor (an ultrasonic receiver) 13 for detecting the ultrasonic wave (reflected wave) reflected by the eye E. The probe 10 is used to measure the intraocular pressure (IOP) of the eye E in non-contact manner. The probe 10 in this embodiment is controlled by a controller 70 to act as the vibrator 11 and the sensor 13. The vibrator 11 and the sensor 13 are not limited to such configuration and may be provided separately.

In FIG. 2, the controller 70 performs calculation of measurement values, control of the entire tonometer, and others. The controller 70 determines the IOP of the eye E by processing output signals of the probe 10. The probe 10 is connected to an amplifier 81. An electrical signal output from the probe 10 is amplified by the amplifier 81 and then input in the controller 70. The controller 70 is also connected to the probe 10, each component of the observation optical system 20 (a light source, the imaging device, etc.), the drive part 6, the monitor 8, a memory 75, and others. The memory 75 stores in advance a measurement program to measure the IOP by use of the probe 10, a control program to control the entire tonometer, and other programs.

Results of an experiment conducted by the inventors are presented below. To capture changes in acoustic characteristics of the cornea due to IOP, a pulse wave was emitted toward a schematic eye (see FIG. 3) by use of the probe 10 and a reflected wave from the schematic eye was detected (see FIG. 4A). Then, the waveform of the detected reflected wave was subject to Fourier analysis to determine the amplitude spectrum of the reflected wave (see FIG. 4B). The inventors focused attention on an amplitude spectrum value of a peak (a peak value) of the amplitude spectrum and evaluated a relationship between the peak value and the IOP (see FIG. 4C). The probe 10 used was a transducer with a nominal frequency of 400 kHz.

Figure 3:
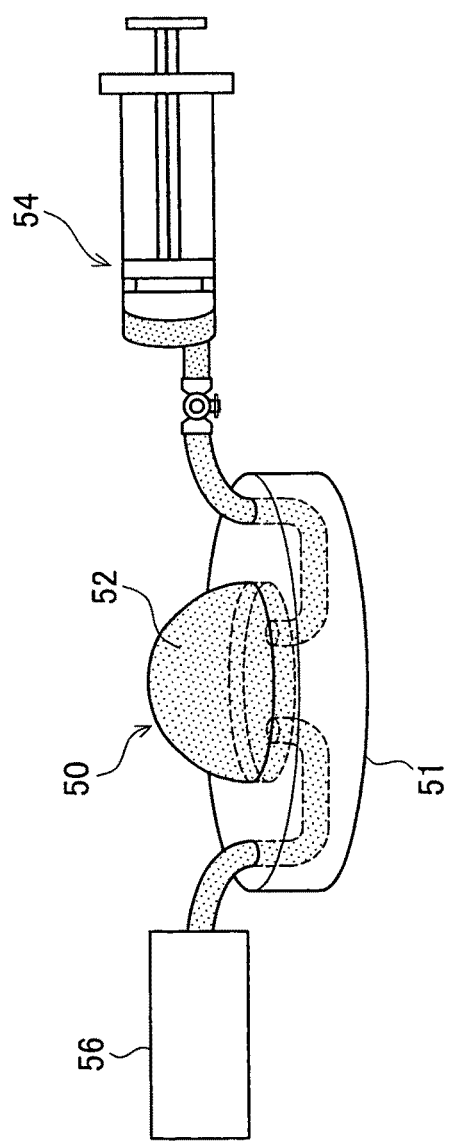
FIG. 3 is a schematic perspective view of an eyeball model (a schematic eye) used in an experiment.

FIG. 3 is a schematic perspective view showing an eyeball model (the schematic eye) used in the experiment. The eyeball model 50 includes a base part 51 and a silicone rubber semispherical element 52 having an internal cavity. The eyeball model 50 is configured such that a fluid is poured in the semispherical element 52 with a syringe 54. The inner pressure of the semispherical element 52 is detected by a manometer 56. In this experiment, the semispherical element 52 is assumed as a cornea and it is conceived that the IOP is changed by adjustment of the inner pressure of the semispherical element 52.

Figure 4C:
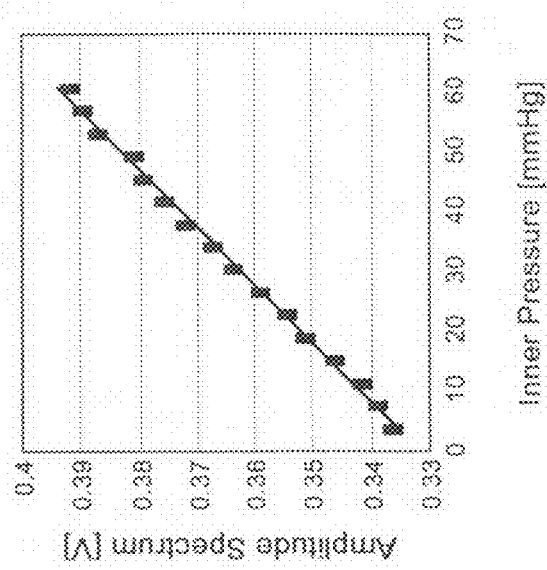
FIGS. 4A to 4C are graphs showing one example of results of the experiment conducted on the eyeball model.
Figure 4B:
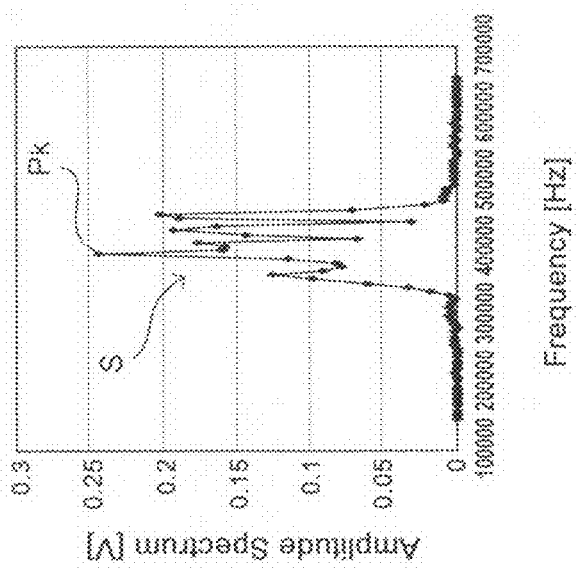
Figure 4A:
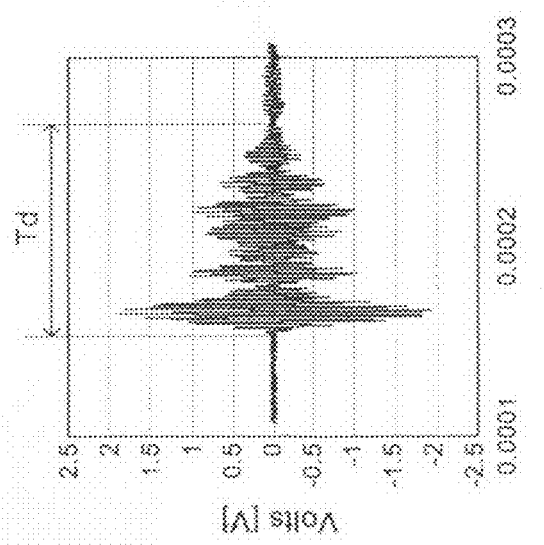

FIGS. 4A to 4C are graphs showing one example of results of the experiment conducted on the eyeball model. Specifically, FIG. 4A is a graph showing temporal changes in amplitude level of the reflected wave detected by the probe 10. In this graph, a lateral axis represents Time and a vertical axis represents Amplitude, and Td denotes a time domain in which a window function (this experiment used a rectangular window) is set in Fourier analysis.

FIG. 4B is a graph showing resolved amplitude level of the reflected wave shown in FIG. 4A per frequency. In this graph, a lateral axis represents Frequency and a vertical axis represents Amplitude, and S denotes amplitude spectrum and Pk denotes a peak of the amplitude level in amplitude spectrum.

FIG. 4C is a graph showing a relationship between the inner pressure of the schematic eye and amplitude spectrum values at the peak P (the peak amplitude level). As shown in FIG. 4C, it is found that the inner pressure of the schematic eye and the amplitude spectrum values are in an almost proportional relationship. This relationship is regarded as being utilizable for measuring IOP.

Figure 5:
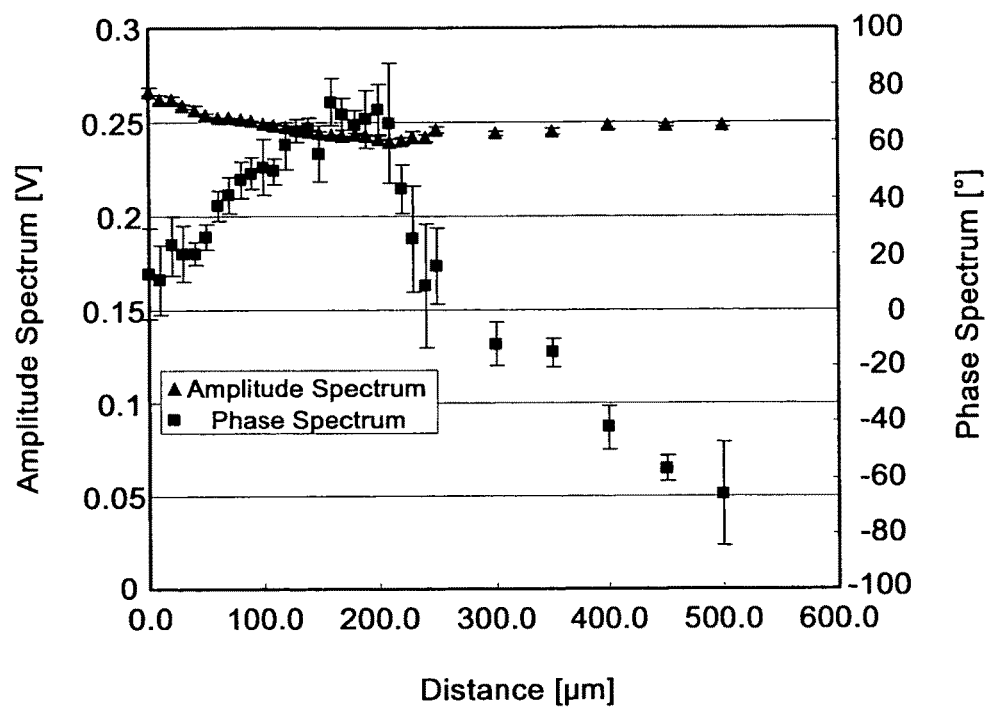
FIG. 5 is a graph showing a relationship between a peak value (Amplitude Spectrum) of amplitude spectrum and an amount of deviation of a working distance and a relationship between a phase change amount (Phase Spectrum) of a reflected wave with respect to an incident wave in a frequency exhibiting a peak in the amplitude spectrum and an amount of amount of the working distance.

FIG. 5 is a graph showing a relationship between a peak value (Amplitude Spectrum) of the amplitude spectrum and an amount of deviation of the working distance and a relationship between a phase change amount (Phase Spectrum) of the reflected wave with respect to the incident wave in the frequency exhibiting a peak in the amplitude spectrum and an amount of deviation of the working distance. In this graph, a lateral axis represents a deviation amount from a predetermined working distance (30 mm).

As shown in FIG. 5, in the case of a peak value in the amplitude spectrum, less variations in measurement results occur due to the changes in working distance. On the other hand, in the case of the phase change amount, variations in measurement results occur due to the changes in working distance. Accordingly, when the IOP is determined relative to the peak in the amplitude spectrum, it is possible to reduce variations in measurement results due to the changes in working distance.

The following explanation is given to a method for measuring IOP in consideration of the above experimental results. The controller 70 causes the probe 10 to emit an ultrasonic pulse toward the eye E and detect the reflected wave resulting from the ultrasonic pulse incident on the eye E. The controller 70 obtains the amplitude spectrum of the reflected wave based on the output signal from the probe 10 and determines the IOP of the eye E based on the peak amplitude level of the amplitude spectrum.

Figure 6:
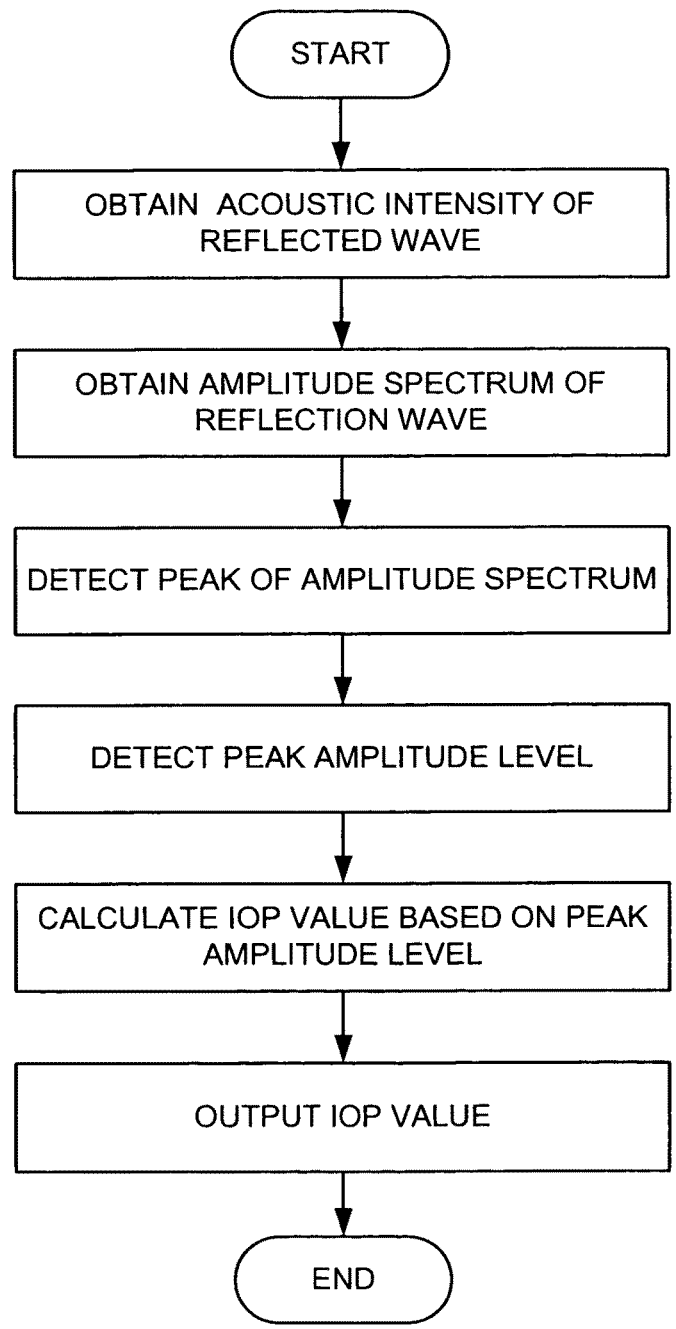
FIG. 6 is a flowchart to explain a concrete example of an IOP measurement method in the embodiment.

FIG. 6 is a flowchart to explain a concrete example of a method for measuring IOP in the present embodiment. When the pulse wave is emitted toward the eye E (the cornea Ec) and the reflected wave is detected by the sensor 13, an electrical signal corresponding to the acoustic intensity (amplitude level) of the reflected wave is output from the sensor 13 and input to the controller 70 through the amplifier 81.

The controller 70 then frequency-analyzes the detected acoustic intensity of the reflected wave (e.g. Fourier analysis) to obtain the amplitude spectrum that is the amplitude level at each frequency in the reflected wave. Furthermore, the controller 70 detects the peak amplitude level of the obtained amplitude spectrum (e.g. a peak value of the amplitude spectrum).

The controller 70 then calculates the LOP based on the peak amplitude level of the amplitude spectrum. The memory 75 stores in advance correlations between the peak amplitude levels and the IOP values. The controller 70 thus retrieves the IOP value corresponding to the detected peak amplitude level from the memory 75 and displays the obtained IOP value on the monitor 8. The correlations between the peak amplitude levels and the IOP values can be set, for example, by previously determining correlations between amplitude levels to be obtained by the present tonometer and IOP values to be obtained by a Goldmann tonometer.

With the above configuration, the IOP measurement using the ultrasonic pulse can provide a stable measurement result. Concretely, since the peak amplitude level of the amplitude spectrum is in a stable state, even when the working distance between the probe 10 and the eye E changes, variations in measurement result due to the changes in working distance can be reduced. Furthermore, the necessity of strict alignment adjustment is mitigated and hence the trouble of alignment adjustment is reduced, thus lessening a burden on the examiner and the examinee.

In the above explanation, the window function used in Fourier analysis of the wave detected by the probe 10 is a rectangular window but not limited thereto. Any window function (e.g. a hanning window, a hamming window, etc.) can be used.

In the above explanation, the peak amplitude level can be precisely detected by detecting the peak in the obtained amplitude spectrum. As an alternative, it also may be arranged to previously determining a frequency (a central frequency) at which the peak of amplitude spectrum is obtained and storing this frequency in the memory 75. In this case, it may be configured to obtain the amplitude level corresponding to the previously set frequency as the peak amplitude level of the amplitude spectrum and calculate the IOP based on this peak amplitude level.

Figure 7:
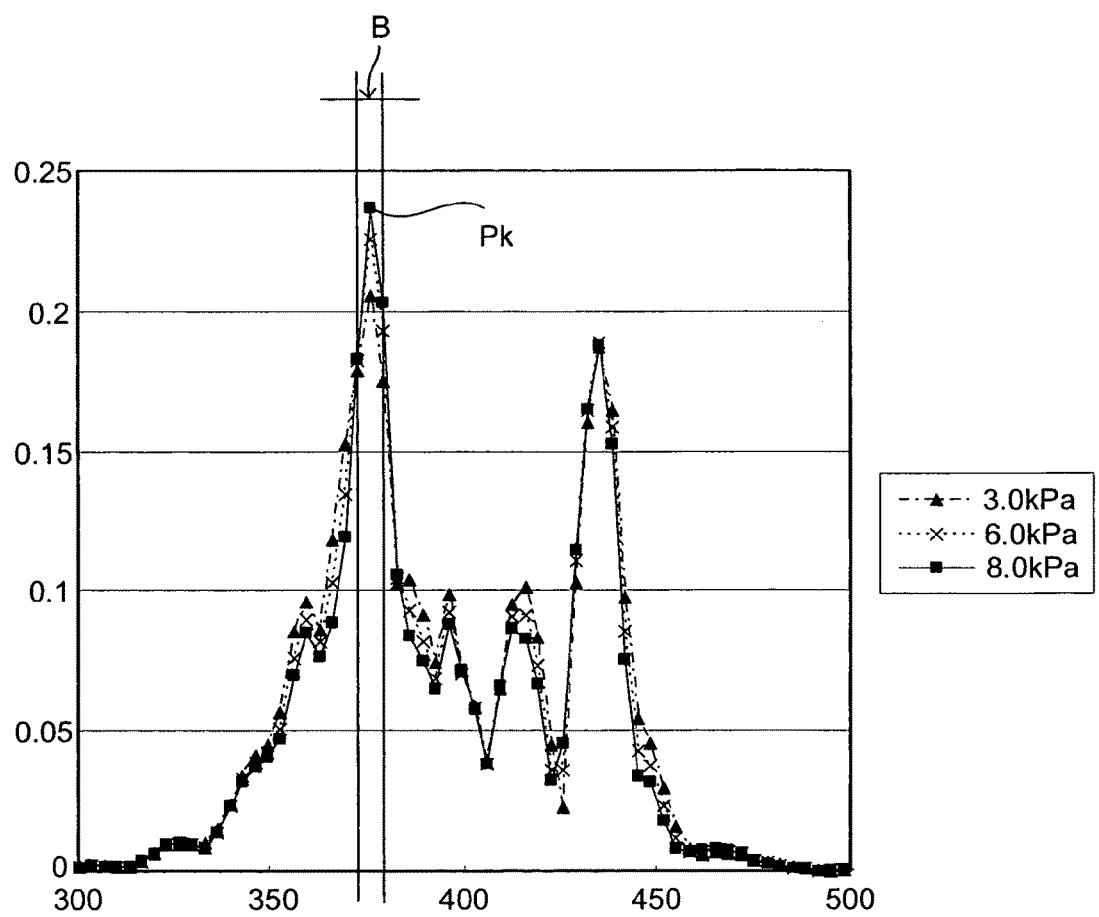
FIG. 7 is a graph showing a relationship between inner pressure of a schematic eye and the amplitude spectrum.

The above explanation uses the peak value of the amplitude spectrum as the peak amplitude level of the amplitude spectrum but not limited thereto. For instance, it may be configured to determine the IOP based on the amplitude level in a predetermined frequency band including the peak in the amplitude spectrum. FIG. 7 is a graph showing a relationship between the inner pressure of the schematic eye and the amplitude spectrum. FIG. 7 reveals that, in a range of ±about 3 kHz from the central frequency (see "B" in FIG. 7), the IOP value is higher as the amplitude level is higher and the IOP value is lower as the amplitude level is lower. The correlation between the amplitude level in that range and the IOP value is similar to the correlation between the peak amplitude level and the IOP value. Therefore, it may be arranged to set, as the predetermined frequency band, a band within the frequency band (see "B" in FIG. 7) in which the same correlation is obtained as that between the peak amplitude level and the IOP value and measure the IOP based on the amplitude level in that frequency band. For instance, an integrated value of the amplitude spectrum in the range of the predetermined frequency set as above and the IOP is measured based on the integrated value. In this configuration, the amplitude level largely changes depending on differences in the IOP value. The IOP can therefore be measured accurately.

In the above explanation, the IOP is determined by use of an arithmetic processing through a software but not limited thereto. The same processing may be conducted by use of a signal processing through a hardware (circuitry). For instance, a conceivable calculation circuit includes an amplitude spectrum detecting circuit (a spectrum analyzer) connected to the probe 10 to obtain a signal of the amplitude spectrum of the reflected wave and a peak hold circuit to detect a peak in the amplitude spectrum obtained by the amplitude spectrum detecting circuit. In this case, the controller 70 calculates the IOP based on the peak amplitude level detected by the peak hold circuit.

Figure 8:
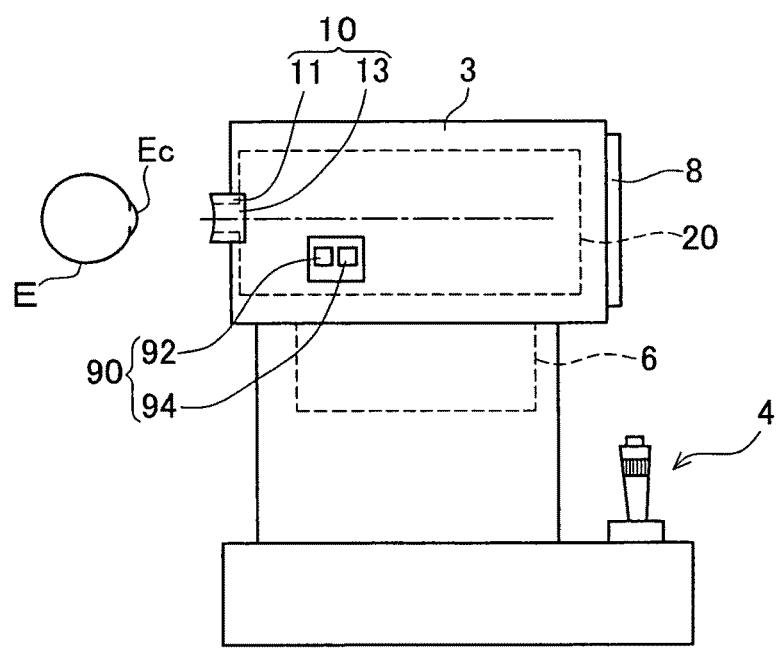
FIG. 8 is a schematic external view showing a state where a temperature and humidity sensor is provided in the tonometer.

FIG. 8 is a schematic external view showing a case where a temperature and humidity sensor is provided in the tonometer. In this case, as a temperature and humidity sensor 90 for detecting the temperature or humidity in air in a measurement environment, a temperature sensor 92 and a humidity sensor 94 are placed. The output of the temperature and humidity sensor 90 is used to correct the IOP value.

The temperature and humidity sensor 90 is located in a place that is not influenced by the examinee or the examiner, direct light, and others, that is, in a position facing the examiner or the examinee during measurement or inside the housing of the tonometer. To detect a state of air near the examinee's eye, on the other hand, the sensor 90 may also be located near the probe 10 (e.g. on a surface of the main unit 3 facing the examinee). The sensor 90 may be configured to change a position thereof according the environment in which the tonometer will be placed.

As an alternative, a plurality of the temperature and humidity sensors 90 may be provided to measure temperature or humidity in air by averaging output values from the sensors, thereby providing a stable measurement result. As another alternative, three or more temperature and humidity sensors 90 may be provided so that a measurement value(s) greatly different from an averaged value of the sensors is removed from calculation of the averaged value.

The temperature and humidity sensor 90 (the temperature sensor 92 and the humidity sensor 94) is connected to the controller 70. The controller 70 measures the temperature and the humidity in air based on output signals from the sensor 90 and utilizes a measurement result thereof to calculate the IOP value.

The present inventors determined an amplitude spectrum of the reflected wave by emitting a pulse wave toward a black silicone rubber by use of the probe 10 and frequency-analyzed the waveform of the reflected wave. This is to determine changes in corneal reflected wave due to the changes in temperature and humidity.

Figure 9A:
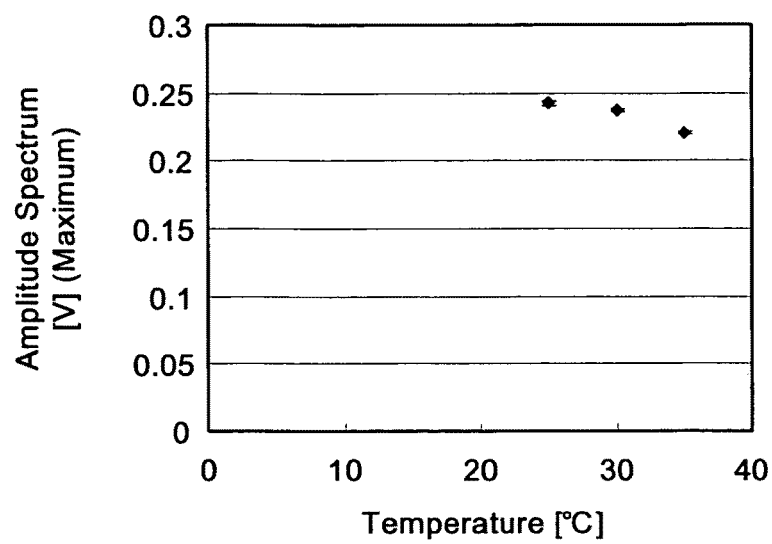
FIGS. 9A and 9B are graphs showing changes in peak value of the amplitude spectrum according to temperature and humidity.
Figure 9B:
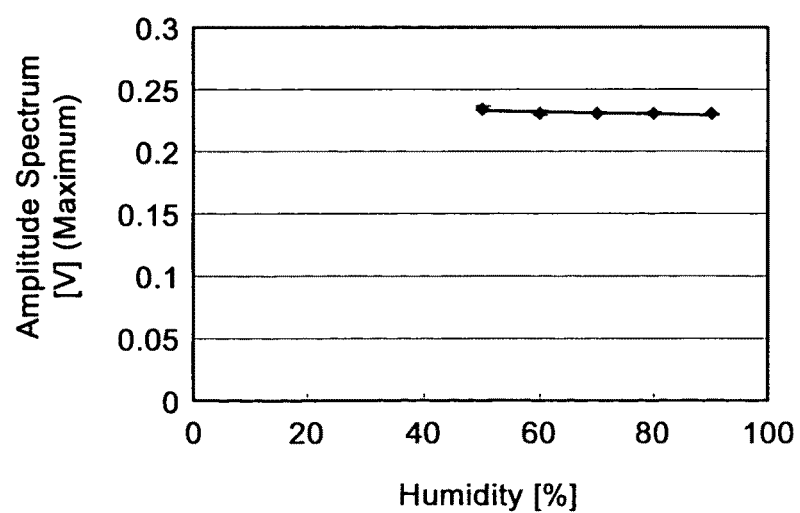

FIGS. 9A and 9B are graphs showing changes in peak value of the amplitude spectrum (see FIG. 4B) according to the temperature and the humidity. FIG. 9A shows a result of temperature change in an environment with constant humidity. In this experiment, the reflected wave was checked under the condition that the humidity was maintained at 65% and the temperature was changed from 25° C. to 35° C. in increments of 5° C. The result revealed that the reflected wave tended to be attenuated as the temperature rises, and the measured IOP was influenced by the temperature changes.

FIG. 9B shows a result of humidity change in an environment with constant temperature. In this experiment, the reflected wave was checked under the condition that the temperature was maintained at 35° C. and the humidity was changed from 50% to 90% in increments of 10%. The result revealed that the reflected wave tended to be attenuated as the humidity rises, and the measured IOP was influenced by the humidity changes. The variation in corneal reflected wave by the humidity changes was smaller than that by the temperature changes.

The following explanation is given to a method for correcting the IOP values measured under the condition that the temperature changes. The sound velocity of ultrasonic wave exhibits a rising tendency and is represented by the following expression (1):

$$c_{AIR} = 331 + 0.6t \tag{1}$$

where $C_{AIR}$ denotes sound velocity in air and t denotes centigrade temperature.

The above expression is an approximation of an expression (2) and can be expressed by:

$$c_{AIR} = \sqrt{\frac{\chi P}{\rho_{AIR}}} = \sqrt{\chi RT} \approx 331 + 0.6t \quad (2)$$

where X denotes a ratio of specific heat at constant pressure and specific heat at constant volume (1.4 in the case of air), P denotes atmospheric pressure, $\rho_{AIR}$ denotes air density, R denotes gas constant (287 J/(kg·K)), and T denotes absolute temperature.

According to the expressions (1) and (2), when the sound velocity increases as the temperature rises, it is conceivable that the acoustic characteristics in air changes.

Acoustic impedance $Z_{AIR}$ in air is expressed by an expression (3):

$$Z_{AIR} = \rho_{AIR} \cdot c_{AIR} \quad (3)$$

Accordingly, it is found that the acoustic impedance in air tends to rise in response to a change in sound velocity $C_{AIR}$ in air.

When thinking the acoustic impedance of a cornea that changes depending on an increase of IOP, the corneal acoustic impedance $Z_C$ is expressed by:

$$Z_c = \rho_c \cdot c_c \quad (4)$$

where $\rho_c$ denotes corneal density and $C_C$ denotes corneal sound velocity.

Herein, $C_C$ is expressed by:

$$c_c = \sqrt{\frac{\kappa}{\rho_c}} \quad (5)$$

where $\kappa$ denotes corneal volume elasticity.

Thus, $Z_C$ is expressed by:

$$Z_c = \rho_c \cdot \sqrt{\frac{\kappa}{\rho_c}} = \sqrt{\rho_c \cdot \kappa} \quad (6)$$

and it is found that $Z_C$ changes by $\kappa$.

Accordingly, a reflectivity R of an ultrasonic wave at the boundary between the air and the cornea is obtained by:

$$R = \frac{Z_c - Z_{AIR}}{Z_c + Z_{AIR}} \quad (7)$$

and it is found that the reflectivity changes according to $Z_C$ and $Z_{AIR}$. At that time, $Z_C$ is a parameter that changes with IOP and will vary according to variations in $Z_{AIR}$, causing a decrease in precision of the IOP value. Thus, the temperature in air is measured and corrected.

Figure 10:
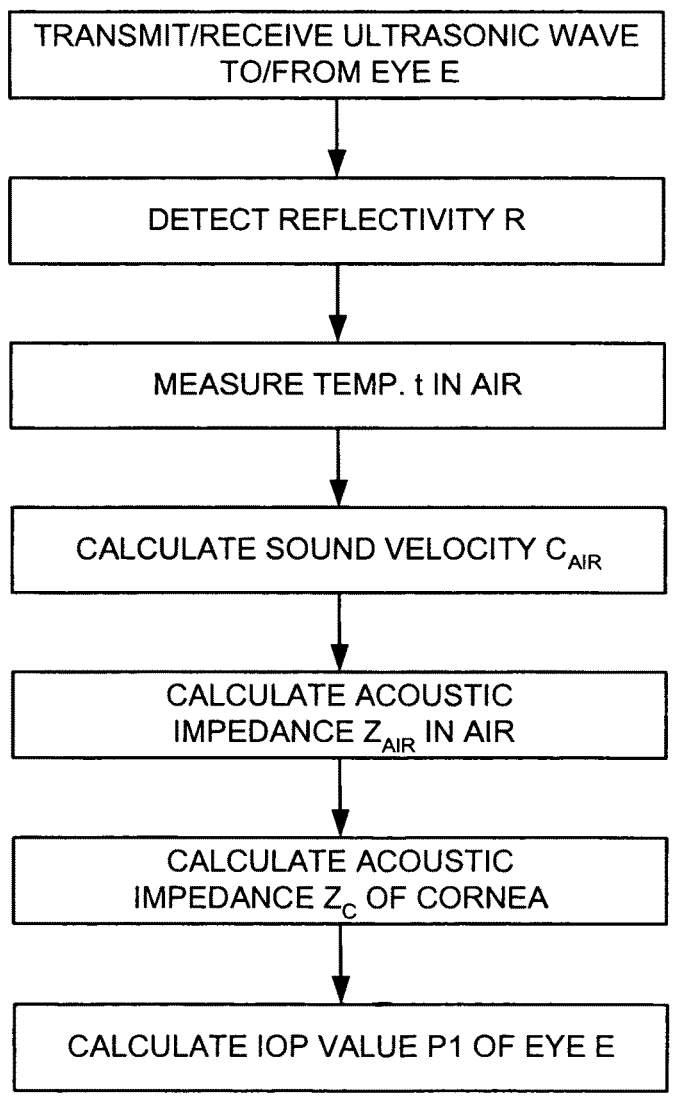
FIG. 10 is a flowchart to explain a method for obtaining IOP values by correcting changes in acoustic impedance in air due to temperature changes.

FIG. 10 is a flowchart to explain a method for obtaining an IOP value by correcting the change in acoustic impedance in air resulting from temperature change.

The controller 70 transmits and receives an ultrasonic wave with respect to the cornea Ec through the probe 10 and detects the reflectivity R of the ultrasonic wave in the cornea Ec. The controller 70 further measures the temperature t in air by use of the temperature sensor 92 and corrects the acoustic impedance $Z_{AIR}$ in air based on the measurement result. The timing of temperature measurement is preferably the same, time as transmittance/reception of the ultrasonic wave or before or after the transmittance/reception. In the case where the tonometer is placed in an environment with less temperature change, it may be arranged to measure the temperature at the time of power-on of the tonometer and at predetermined time intervals (e.g. every ten minutes).

The reflectivity R of the cornea Ec is determined by for example an amplitude spectrum Pi of a transmitted wave in the transmitter 11 and an amplitude spectrum Pr of a reflected wave in the receiver 13 (R=Pr/Pi). The reflectivity R can also be determined from peaks in the amplitude spectrums of the transmitted wave and the received wave. Another alternative is to determine an amplitude spectrum of the reflected wave in the receiver 13 under the assumption that an amplitude spectrum Pi of the transmitted wave is known.

When the temperature t in air in the measurement environment is determined by the temperature sensor 92, the sound velocity $c_{AIR}$ in air is calculated by the above expression (1) or (2). After the sound velocity $c_{AIR}$ is determined, the acoustic impedance $Z_{AIR}$ in air is corrected by use of the above expression (3). Thus, the acoustic impedance $Z_{AIR}$ in air is corrected according to the measurement environment.

When the reflectivity R is calculated and the acoustic impedance $Z_{AIR}$ in air is corrected, the controller 70 calculates the acoustic impedance $Z_C$ of the cornea Ec by use of the above expression (7), and a IOP value P1 of the eye E is calculated based on the calculated acoustic impedance $Z_C$. It is to be noted that the acoustic impedance $Z_C$ and the IOP of the examinee's eye are in a proportional relationship, so that the IOP is smaller as $Z_C$ is smaller and the IOP is larger as $Z_C$ is larger. The controller 70 thus obtains the IOP value P1 of the examinee's eye by utilizing the above relationship.

With the above configuration, it is possible to obtain a proper IOP value irrespective of the change in corneal reflected wave due to the temperature changes. The IOP can be measured according to changes in the measurement environment. Since the influence of the temperature change on the IOP value is larger the influence of the humidity change on the same as described above, it may be arranged to make only correction in response to the temperature change as explained above.

The correction processing may be conducted in association with humidity changes. The controller 70 measures the temperature by using the temperature sensor 92 as above and also measures the humidity in air in the measurement environment by using the humidity sensor 94 to correct the IOP value P1 based on the measurement result. The timing of humidity measurement can be made synchronous with the timing of the above temperature measurement.

Figures 11, 12:
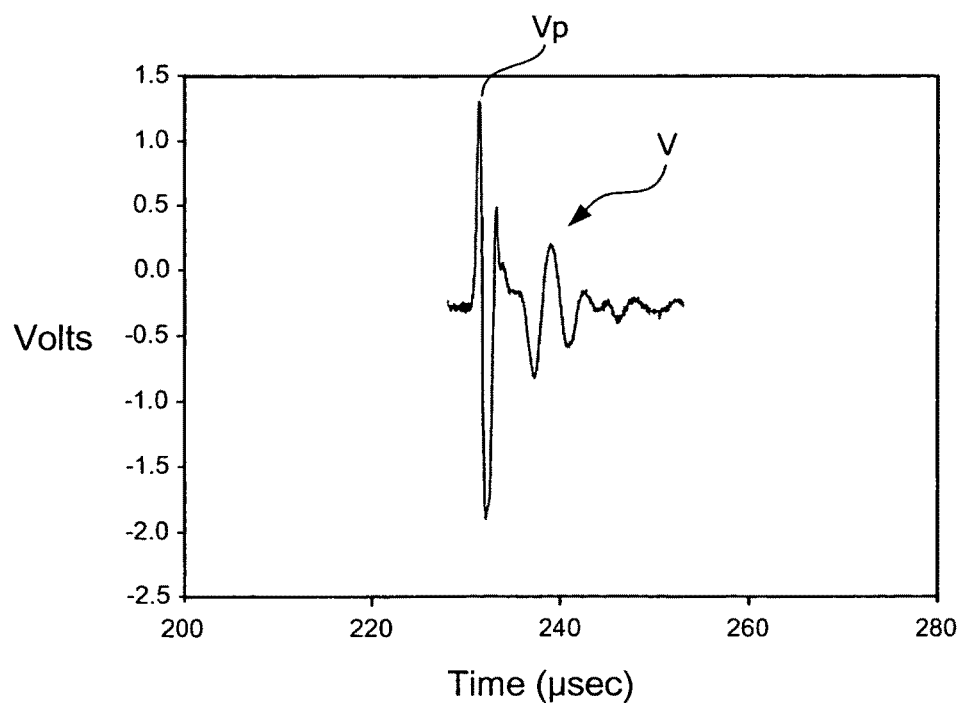
FIG. 11 is a correction table corresponding to combinations of IOP values and humidity.
FIG. 12 a graph showing temporal changes in acoustic intensity of a reflected wave detected by a probe.

Herein, the IOP value P1 is a measured value obtained after the correction associated with the temperature change and before the correction associated with the humidity change. The memory 75 has stored in advance a table of correction values Pc (P1, h) corresponding to combinations of IOP values P1 and humidity h as shown in FIG. 11. When correction is needed, a correction value is selected from this table. An IOP value P2 of the examinee's eye after the correction is calculated by the calculation of P2=P1+Pc (P1, h) and displayed on the monitor 8.

When the above correction table is to be created, for example, the schematic eye having a predetermined IOP is measured in advance under a predetermined humidity condition and a correction value is obtained based on the amount of deviation of the measured values when the humidity is changed. This is made on the schematic eyes having different IOP values to create a table per IOP value.

Not only the above method but also the following method may be adopted. Specifically, a regression expression showing changes in reflectivity R according to humidity is created in advance by use of the experimental results shown in FIG. 9. After correction of the reflectivity R by the regression expression, the IOP value P2 is calculated based on the corneal acoustic impedance $Z_C$.

With the above configuration, a proper IOP value can be obtained irrespective of the changes in corneal reflected wave associated with the temperature and humidity rise. This enables the IOP measurement according to the changes in measurement environment.

In the above explanation, the IOP is calculated by correcting the acoustic impedance based on the output signal from the temperature sensor 92, but the invention is not limited thereto. The correction table as used for correction of the humidity change may be created. For instance, a table of correction values corresponding to combinations of each IOP value obtained under predetermined temperature conditions and each temperature t is stored in the memory 75. The controller 70 calculates an IOP value based on the IOP value measured based on the output of the probe 10 and the temperature t measured based on the output of the temperature sensor 92.

In the above configuration, the temperature t and the humidity h measured by the temperature and humidity sensor 90 may be displayed on the monitor 8.

In the above configuration, the sound velocity $c_{AIR}$ in air is indirectly calculated by use of the temperature and humidity sensor 90. An alternative is to directly calculate the sound velocity in air by use of a sound velocity sensor to correct the acoustic impedance $Z_{AIR}$ in air. As the sound velocity sensor, for example, the probe 10 is also used as the sound velocity sensor. The controller 70 calculates the sound velocity in air based on the time needed for the ultrasonic wave transmitted toward the schematic eye having a predetermined IOP value returns to the probe 10.

The above correction processing associated with the temperature and humidity changes may be applied to another measuring method if only it is to measure IOP by utilizing characteristics and waveforms of corneal reflected wave changing with the IOP of the examinee's eye. For instance, it is applicable to a measurement method for determining a IOP value by analyzing the corneal reflected wave to detect a phase difference between the phase of an incident wave and the phase of a reflected wave and thereby calculating a reflectivity based on the phase difference.

The probe 10 (an ultrasonic transmitter-receiver) is preferably an air-coupled ultrasonic probe for transmitting and receiving an ultrasonic beam having a frequency component of a broad band is used to increase a propagation efficiency in air. For instance, it generates an ultrasonic wave of a broad band having a frequency band from about 200 kHz to 1 MHz. In this case, a BAT™ probe offered by Microacoustic can be used. The details of such probe are referred to U.S. Pat. No. 5,287,331 and JP 2005-506783 A, for example.

According to the above configuration, the propagation efficiency of the ultrasonic wave in air can be enhanced and furthermore the influence of reverberant noise is greatly reduced. It is possible to ensure a very higher S/N ratio (about 100 times or more) compared with a commercially available piezoelectric ultrasonic probe. Accordingly, even if the predetermined working distance is long (e.g. 10 mm or more) at the time of completion of alignment with respect to the examinee's eye, the peak amplitude level of the amplitude spectrum can be detected at a high S/N ratio, enabling IOP measurement with high precision.

In the above explanation, the IOP is calculated based on the peak amplitude level of the amplitude spectrum. An alternative is to calculate the IOP based on the peak amplitude level of the reflected wave.

FIG. 12 is a graph showing temporal changes in acoustic intensity of the reflected wave detected by the probe 10. In this graph, V denotes the acoustic intensity and Vp denotes a peak in the acoustic intensity. FIG. 12 shows the acoustic intensity of the reflected wave output from the probe 10 in the case of using the broad-band and air-coupled ultrasonic probe.

The controller 70 detects a peak amplitude level of the acoustic intensity V (e.g. a peak value Vp of the acoustic intensity) in the reflected wave based on the output signal from the probe 10 and then calculates the IOP based on that peak amplitude level. It may be arranged to detect, as the peak amplitude level, an integrated value of the acoustic intensity in a predetermined time including the peak of the acoustic intensity.

It is experimentally confirmed that the peak value Vp of the acoustic intensity V does not change according to the deviation amount of the predetermined working distance (30 mm) as in the case shown in FIG. 5. Furthermore, it is experimentally confirmed that the influences of temperature and humidity are similar to those in FIG. 9.

With the above configuration, it is unnecessary to obtain the amplitude spectrum by Fourier analysis or the like, so that a calculating process can be simplified and a calculation software, a calculation circuitry, and others can be simplified.

In the case of determining the IOP from the relationship between the peak amplitude level and the acoustic impedance of the cornea of the examinee's eye, the aforementioned reflectivity R can be determined by the acoustic intensity of the transmitted wave in the transmitter 11 and the acoustic intensity of the reflected wave in the receiver 13. The reflectivity may also be determined from the peaks of the acoustic intensity of the transmitted wave and the received wave. Another alternative is determine the acoustic intensity of the reflected wave in the receiver 13 under the assumption that the acoustic intensity of the transmitted wave is known.

In the case of calculating the IOP based on the acoustic intensity, the IOP is determined based on a detection signal including a frequency band deviated from the central frequency. It is therefore relatively difficult to ensure a good S/N ratio.

It is therefore preferable to use the aforementioned broadband and air-coupled ultrasonic probe. This configuration can enhance the propagation efficiency of the ultrasonic wave in air and further greatly reduce the influence of reverberant noise. It is accordingly possible to ensure a very high S/N ratio (about 100 times or more) compared with the commercially available piezoelectric ultrasonic probe. Even when the IOP is calculated based on the peak amplitude level of the acoustic intensity, consequently, a sufficient S/N ratio can be ensured. This enables IOP calculation with high precision based on the acoustic intensity.

Figure 13:
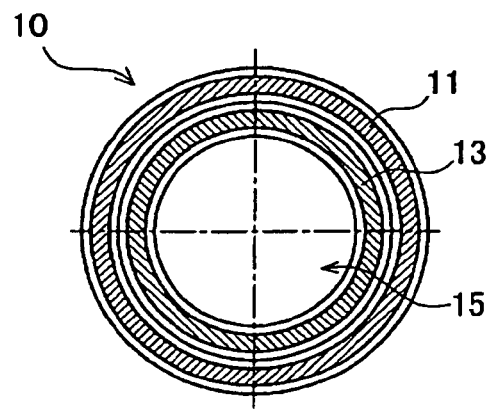
FIG. 13 is a view showing a case of using a ring probe.

A preferable probe as the probe 10 includes an aperture 15 having a sufficient size for observation of the examinee's eye as shown in FIG. 13, a transmitter 11 and a receiver 13 for an ultrasonic beam, which are placed around the aperture 15. An observation optical system 20 is placed behind the aperture 15. This configuration can ensure the areas of the transmitter 11 and the receiver 13, so that a S/N ratio of a detection signal of a corneal reflected wave detected by the probe 10 can be increased.

Figure 14:
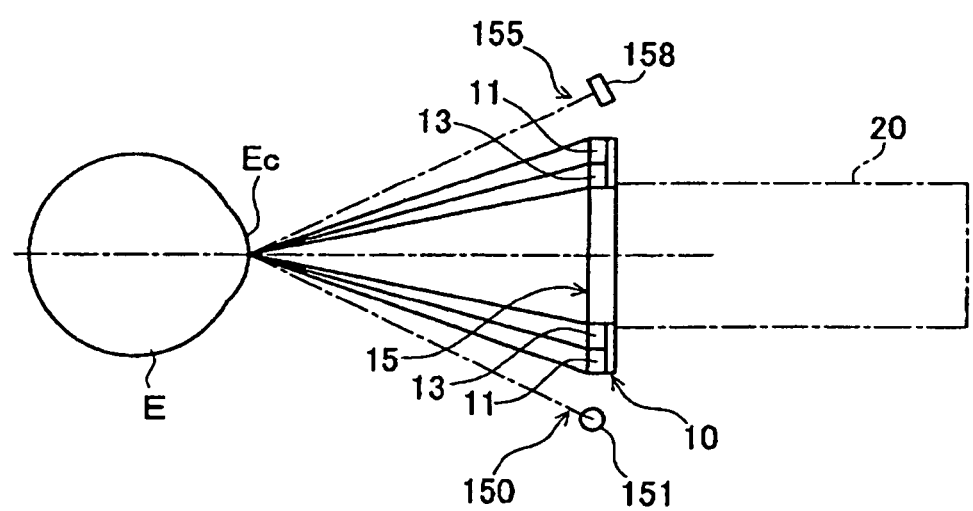
FIG. 14 is a view showing a case where a detecting optical system is provided to detect an alignment state in a working distance direction.

The above configuration may also be provided with a light projecting optical system for projecting alignment light to the examinee's eye and a light receiving optical system for receiving reflected light thereof, serving as a detection optical system to detect an alignment state of the tonometer in the working distance (forward and backward) directions. For instance, as shown in FIG. 14, it is conceivable to provide a light projecting optical system 150 including a light source 151 and configured to obliquely project a target onto the examinee's eye and a light receiving optical system 155 including a position detecting element 158 and configured to detect an image of the target formed on the cornea by the light projecting optical system 150.

In this case, the controller 70 detects an alignment state in the working distance direction based on an output signal from the position detecting element 158. Based on a detection result thereof, the controller 70 then judges whether the working distance between the cornea and the probe 10 is a predetermined working distance or not and appropriate or not. The controller 70 thus obtains an IOP value based on the judgment result. For instance, when the working distance is judged appropriate, an ultrasonic pulse is emitted. Alternatively, an ultrasonic pulse is continuously emitted and an IOP value is obtained based on the characteristics of a corneal reflected wave obtained when the distance is judged appropriate.

The controller 70 may also be configured to make automatic alignment for controlling driving of the drive part 6 based on the detection result and display a guidance display on the screen of the monitor 8.

The above configuration makes it possible to smoothly make alignment and measuring start operations to detect the peak amplitude level of the corneal reflected wave in the predetermined working distance.

While the presently preferred embodiment of the present invention has been shown and described, it is to be understood that this disclosure is for the purpose of illustration and that various changes and modifications may be made without departing from the scope of the invention as set forth in the appended claims.

The invention claimed is:

1. A non-contact ultrasonic tonometer for measuring an intraocular pressure of an examinee's eye in non-contact manner by use of an ultrasonic wave, comprising:
    an ultrasonic transducer including a transmitter which emits an ultrasonic transmission pulse wave to the eye and a receiver which detects an ultrasonic reflection pulse wave from the eye, the transducer being arranged to be placed in a position apart from the eye and to transmit and receive the pulse wave with respect to the eye through the medium of air; and
    a detection optical system for detecting an alignment state of the tonometer with respect to the eye in a working distance direction;
    a drive part to move a main unit in which the ultrasonic transducer is provided with respect to the eye; and
    a controller configured to detect an alignment state of the main unit in the working distance direction based on a detection result of the alignment detection optical system, determine whether a distance between the ultrasonic transducer and the eye is appropriate or not based on the detection result, and measure the intraocular pressure based on the ultrasonic reflection pulse wave when the distance is determined to be appropriate,
    wherein the distance between the ultrasonic transducer and the eye is appropriate if the distance falls within a predetermined range.

2. The ultrasonic tonometer according to claim 1, wherein the controller continuously emits the ultrasonic transmission pulse wave and measures the intraocular pressure based on the ultrasonic reflection pulse wave obtained when the distance is determined to be appropriate.

3. The ultrasonic tonometer according to claim 1, wherein the controller controls driving of the drive part based on the detection result of the alignment state and adjusts the distance between the ultrasonic transducer and the eye to a predetermined working distance.

4. The ultrasonic tonometer according to claim 1, wherein the controller emits the ultrasonic transmission pulse wave when the distance is determined to be appropriate.

5. The ultrasonic tonometer according to claim 1, wherein the detection optical system includes a light projecting optical system for projecting alignment light to the eye, and a light receiving optical system for receiving reflected light of the alignment light from the eye.

6. The ultrasonic tonometer according to claim 1, wherein the controller measures the intraocular pressure based on a peak amplitude level of the ultrasonic reflection pulse wave.

7. The ultrasonic tonometer according to claim 1, wherein the controller obtains an amplitude spectrum by frequency-analysis of acoustic intensity of the ultrasonic reflection pulse wave and measures the intraocular pressure based on the obtained amplitude spectrum.

\* \* \* \* \*